United States Patent
Ku (10) Patent No.: US 9,687,164 B2
(45) Date of Patent: Jun. 27, 2017

(54) METHOD AND SYSTEM FOR SIGNAL ANALYZING AND PROCESSING MODULE

(71) Applicant: MEDIATEK INC., Hsin-Chu (TW)

(72) Inventor: Po-Wen Ku, Hsinchu County (TW)

(73) Assignee: MEDIATEK INC., Hsin-Chu (TW)

( * ) Notice: Subject to any disclaimer, the term of this patent is extended or adjusted under 35 U.S.C. 154(b) by 414 days.

(21) Appl. No.: 13/873,202

(22) Filed: Apr. 29, 2013

(65) Prior Publication Data

US 2014/0323890 A1 Oct. 30, 2014

(51) Int. Cl.
*A61B 5/04* (2006.01)
*A61B 5/00* (2006.01)
*A61B 5/0428* (2006.01)

(52) U.S. Cl.
CPC ........ *A61B 5/04017* (2013.01); *A61B 5/0428* (2013.01); *A61B 5/7203* (2013.01); *A61B 5/725* (2013.01); *A61B 5/7207* (2013.01)

(58) Field of Classification Search
CPC . A61B 5/0402; A61B 5/0452; A61B 5/04012; A61B 5/0422; A61B 5/0245; A61B 5/7246; A61B 5/7275; A61B 5/04017; A61B 5/7203; A61B 5/7207; A61B 5/04525; A61B 5/11; A61B 5/6801; A61B 5/7282; A61B 5/721; A61B 5/046; A61B 5/053; A61N 1/39
USPC ......................................................... 600/509
See application file for complete search history.

(56) References Cited

U.S. PATENT DOCUMENTS

| | | | |
|---|---|---|---|
| 4,627,441 A | 12/1986 | Martin | |
| 4,799,493 A * | 1/1989 | DuFault | 600/518 |
| 5,671,752 A * | 9/1997 | Sinderby et al. | 600/546 |
| 5,704,365 A * | 1/1998 | Albrecht et al. | 600/515 |
| 6,547,746 B1 * | 4/2003 | Marino | 600/554 |
| 7,963,283 B2 * | 6/2011 | Sinderby | 128/204.23 |
| 9,089,310 B2 * | 7/2015 | Isenhart et al. | 600/544 |
| 2004/0243015 A1 * | 12/2004 | Smith et al. | 600/511 |
| 2007/0156190 A1 * | 7/2007 | Cinbis | 607/5 |
| 2007/0213626 A1 * | 9/2007 | John et al. | 600/509 |
| 2008/0069375 A1 * | 3/2008 | Lange | 381/94.4 |

(Continued)

OTHER PUBLICATIONS

V. Almenar et al., A new adaptive scheme for ECG enhancement, 1999, pp. 253-263, XP004166444, Elsevier Science B. V.

(Continued)

*Primary Examiner* — Christopher D Koharski
*Assistant Examiner* — Jeremiah Kimball
(74) *Attorney, Agent, or Firm* — Winston Hsu (57) ABSTRACT

Embodiments of the invention disclose a method and a system for signal analyzing and a processing module of the system. The signal analyzing system includes a plurality of first electrodes, a plurality of second electrodes, and a processing module. The first electrodes transmit a plurality of first input signals. The second electrodes transmit a plurality of second input signals. The processing module generates a body electrical signal according to at least one of the plurality of first input signals and at least one of the plurality of second input signals, generates a first filtered signal corresponding to the plurality of first input signals, generates a second filtered signal corresponding to the plurality of second input signals, and generates a lead signal according to the body electrical signal, the first filtered signal and the second filtered signal.

21 Claims, 9 Drawing Sheets

(56) References Cited

U.S. PATENT DOCUMENTS

2011/0190598 A1* 8/2011 Shusterman .................. 600/301
2012/0157867 A1* 6/2012 Pekonen ....................... 600/509

OTHER PUBLICATIONS

Jeong-Whan Lee et al., Reusable Electrical Activity of the Heart Monitoring Patch for Mobile/Ubiquitous Healthcare, Jun. 25, 2008, pp. 41-46, XP019681707, Springer Science + Business Media, LLC.

* cited by examiner

METHOD AND SYSTEM FOR SIGNAL ANALYZING AND PROCESSING MODULE

BACKGROUND

1. Technical Field

The invention generally relates to a method and a system for signal analyzing and a processing module of the system, and more particularly, to a method and a system for signal analyzing and a processing module of the system which can filter noise components according to multiple input signals.

2. Description of Related Art

With the development of biomedical engineering, doctors can make convincing diagnoses according to all sorts of medical reports produced by biomedical inspection instruments. For example, the instruments may obtain a physiological signal, such as an electrocardiogram (ECG) signal, through electrodes directly attached to a patient's chest, arm, or leg. Then, the amplitude of the physiological signals can be measured and transmitted to other circuitry for processing.

Typically, the amplitude the ECG signal transmitted from electrodes is usually measured around millivolts, so that noise components within the ECG signal may play a significant role in affecting the actual waveform of the ECG signal. Thus, it is meaningless to analyze the ECG signal with the presence of noise components in the ECG waveforms. In order to reduce the noise components within the ECG signal, high pass filters or band pass filters are generally used to reduce the noise components caused by external factors, such as power-line interference, ambient electromagnetic activity or movements of electrodes. Practically, reducing the noise components of the ECG signal which is caused by physiological processes within the patient is a critical issue nowadays, and it is worthy to develop a signal analyzing system and a signal analyzing method which can filter out the noise components.

SUMMARY

According to an embodiment of the invention, a signal analyzing method including the following steps is disclosed. First, a body electrical signal is generated according to at least one of a plurality of first input signals and at least one of a plurality of second input signals. Then, a first filtered signal corresponding to the plurality of first input signals is generated. And, a second filtered signal corresponding to the plurality of second input signals is also generated. Further, a lead signal is generated according to the body electrical signal, the first filtered signal and the second filtered signal. To be noted, the plurality of first input signals are transmitted from a plurality of first electrodes of a first electrode group, and the second input signals are transmitted from a plurality of second electrodes of a second electrode group.

According to another embodiment of the invention, a signal analyzing system is disclosed. The signal analyzing system includes a first electrode group having a plurality of first electrodes, a second electrode group having a plurality of second electrodes, and a processing module. The plurality of first electrodes is configured to transmit a plurality of first input signals. The plurality of second electrodes is configured to transmit a plurality of second input signals. The processing module includes a first calculating unit, a second calculating unit, a third calculating unit and a fourth calculating unit. The first calculating unit is coupled to the first electrode group and the second electrode group for receiving at least one of the plurality of first input signals and at least one of the plurality of second input signals. The first calculating unit is configured to generate a body electrical signal according to at least one of the first input signals and at least one of the second input signals. The second calculating unit is coupled to the first electrode group for receiving the plurality of first input signals, and is configured to generate a first filtered signal by filtering a first difference signal corresponding to the plurality of first input signals. The third calculating unit is coupled to the second electrode group for receiving the plurality of second input signals, and is configured to generate a second filtered signal by filtering a second difference signal corresponding to the plurality of second input signals. The fourth calculating unit is coupled to the first calculating unit, the second calculating unit and the third calculating unit for receiving the body electrical signal, the first filtered signal and the second filtered signal, and is configured to generate a lead signal according to the body electrical signal, the first filtered signal and the second filtered signal.

According to the other embodiment of the invention, a processing module is disclosed and configured to generate a lead signal according to a plurality of first input signals transmitted from a plurality of first electrodes, and according to a plurality of second input signals transmitted from a plurality of second electrodes. The processing module includes a first calculating unit, a second calculating unit, a third calculating unit, and a fourth calculating unit. The first calculating unit is coupled to the first electrode group and the second electrode group for receiving at least one of the plurality of first input signals and at least one of the plurality of second input signals. The first calculating unit is configured to generate a body electrical signal according to at least one of the first input signals and at least one of the second input signals. The second calculating unit is coupled to the first electrode group for receiving the plurality of first input signals, and is configured to generate a first filtered signal by filtering a first difference signal corresponding to the plurality of first input signals. The third calculating unit is coupled to the second electrode group for receiving the plurality of second input signals, and is configured to generate a second filtered signal by filtering a second difference signal corresponding to the plurality of second input signals. The fourth calculating unit is coupled to the first calculating unit, the second calculating unit and the third calculating unit for receiving the body electrical signal, the first filtered signal and the second filtered signal, and is configured to generate a lead signal according to the body electrical signal, the first filtered signal and the second filtered signal.

In order to further the understanding regarding the invention, the following embodiments are provided along with illustrations to facilitate the disclosure of the invention.

DETAILED DESCRIPTION

The aforementioned illustrations and following detailed description are exemplary for the purpose of further explaining the scope of the invention. Some objectives and advantages related to the invention will be illustrated in the subsequent description and appended drawings.

Figure 1:
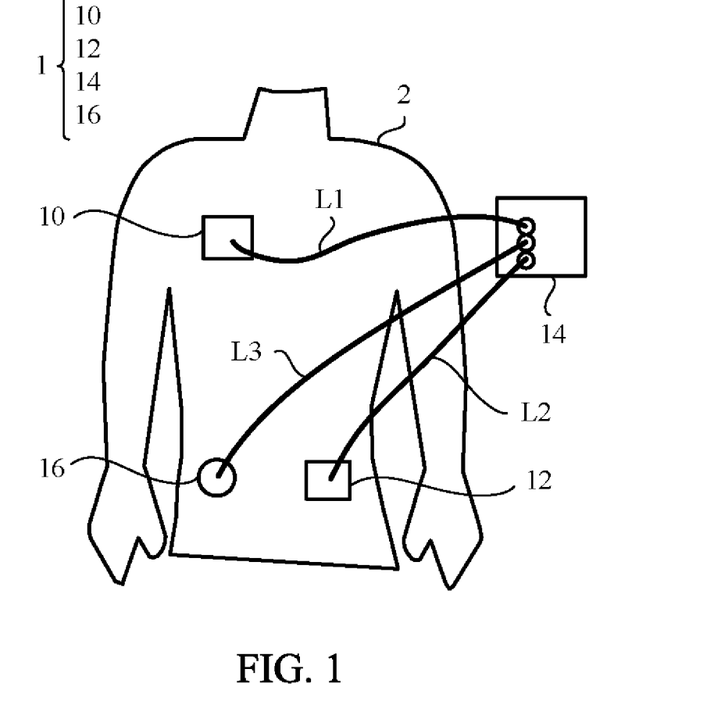
FIG. 1 shows a schematic diagram of a signal analyzing system according to an embodiment of the invention.
Figure 2:
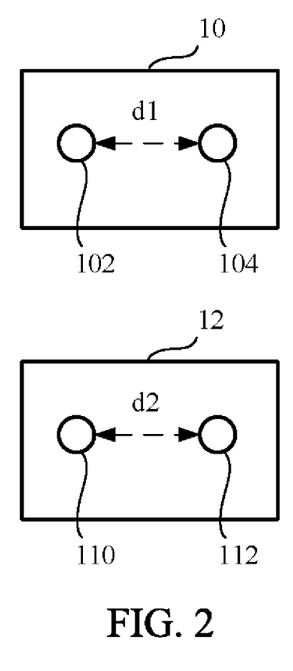
FIG. 2 shows a schematic diagram of a first electrode group and a second electrode group of FIG. 1 according to an embodiment of the invention.
Figure 3:
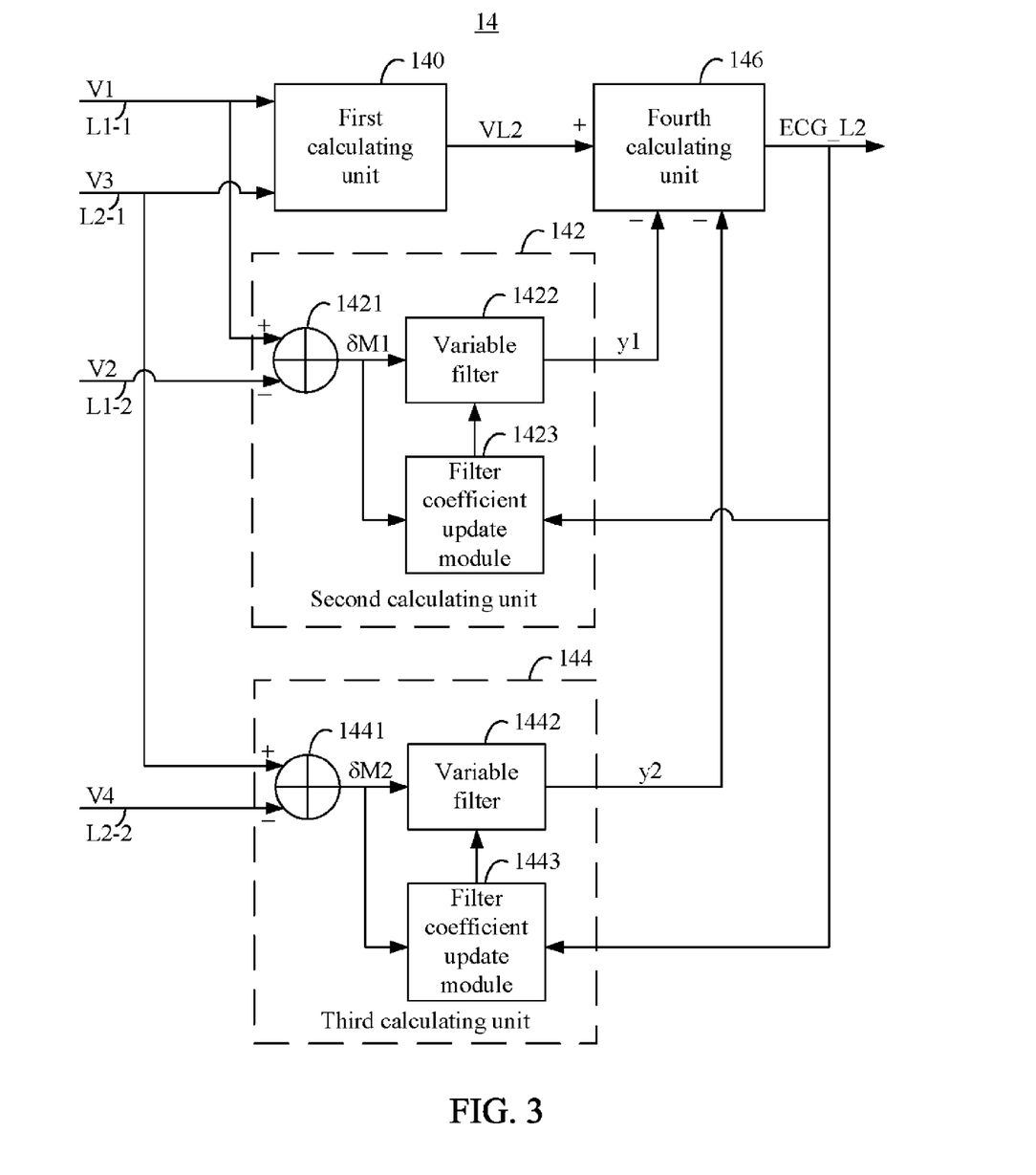
FIG. 3 shows a circuit diagram of a processing module of the signal analyzing system according to an embodiment of the invention.

Please refer to FIG. 1, FIG. 2, and FIG. 3. FIG. 1 shows a schematic diagram of a signal analyzing system according to an embodiment of the invention. FIG. 2 shows a schematic diagram of a first electrode group and a second electrode group of FIG. 1 according to an embodiment of the invention. FIG. 3 shows a circuit diagram of a processing module of the signal analyzing system according to an embodiment of the invention. As shown in figures, a signal analyzing system 1 has a first electrode group 10, a second electrode group 12, a processing module 14, and a bias electrode 16. The first electrode group 10 has a plurality of electrodes (first electrodes), and those electrodes are attached to a human body 2. The second electrode group 12 also has a plurality of electrodes (second electrodes), and those electrodes are also attached to the human body 2.

In practice, the first electrode group 10 and the second electrode group 12 may be attached to different areas of the human body 2. For example, the first electrode group 10 can, but is not limited to, be attached to the right chest of the human body 2, and the second electrode group 12 can, but is not limited to, be attached to the left abdomen of the human body 2. The present embodiment does not limit how the first electrode group 10 and the second electrode group 12 are attached to the human body 2. For example, the first electrode group 10 can be attached to the skin of the human body 2 with an electrically conductive gel, so that the first electrode group 10 can obtain signals easily.

As shown in the FIG. 1, FIG. 2 and the related description thereof, the first electrode group 10 of this embodiment has a first electrode 102 and a second electrode 104. The first electrode 102 and the second electrode 104 are disposed within a first predetermined distance, e.g. 1 cm or 1.5 cm. In other words, the distance d1 depicted in FIG. 2 is less than or equal to the first predetermined distance. Similarly, the second electrode group 12 of this embodiment can also have two electrodes, including a third electrode 110 and a fourth electrode 112, and the electrodes of the second electrode group 12 shall be disposed within a second predetermined distance. In other words, the distance d2 depicted in FIG. 2 is less than or equal to the second predetermined distance. The present embodiment does not limit whether the second predetermined distance is the same as the first predetermined distance. For example, the second predetermined distance may also be 1 cm or 1.5 cm.

The first electrode 102 is configured to transmit a first input signal V1 obtained from the human body 2 to the processing module 14 through a transmission wire L1-1. The second electrode 104 is configured to transmit a second input signal V2 obtained from the human body 2 to the processing module 14 through a transmission wire L1-2. Specifically, the transmission wire L1-1 and the transmission wire L1-2 are collectively called first transmission line pair L1. The wires of the first transmission line pair L1 may be isolated from each other to reduce signal interference. Similarly, the third electrode 110 is configured to transmit a third input signal V3 obtained from the human body 2 to the processing module 14 through a transmission wire L2-1. The fourth electrode 112 is configured to transmit a fourth input signal V4 obtained from the human body 2 to the processing module 14 through a transmission wire L2-2. Specifically, the transmission wire L2-1 and the transmission wire L2-2 are collectively called second transmission line pair L2. The wires of the second transmission line pair L2 may be isolated from each other to reduce signal interference.

In practice, every input signal transmitted from the first electrode group 10 and the second electrode group 12 may not be an ideal signal. And each of the input signals can be considered to have two major components, such as an ECG component and a noise component. Because the first electrode 102 and the second electrode 104 of the first electrode group 10 are attached adjacently, the first electrode 102 and the second electrode 104 may receive the same first ECG component ECG_1. However, different electrodes would transmit different input signals due to the variation of the noise components. Similarly, because the third electrode 110 and the fourth electrode 112 of the second electrode group 12 are attached adjacently, the third electrode 110 and the fourth electrode 112 may receive the same third ECG component ECG_3.

To be noted, it is beneficial that the signal analyzing system 1 can further have the bias electrode 16 for providing DC content within the signals collected by the first electrode group 10 and/or the second electrode group 12. For example, the DC content can be considered as an isoelectric point corresponding to a zero voltage reference. However, those skilled in the art shall understand that the signal analyzing system 1 can still have acceptable results without the bias electrode 16.

As mentioned above, the first electrode 102 may detect the first input signal V1 from the human body 2, and the second electrode 104 may detect the second input signal V2 from the human body 2. The first input signal V1 and the second input signal V2 can be presented as the formulas listed below:

$$V1 = ECG\_1 + M1 \qquad (1)$$

$$V2 = ECG\_1 + M2 \qquad (2)$$

ECG_1 represents the ECG component in the first input signal V1; M1 represents the noise component, especially motion artifact, in the first input signal V1. In this embodiment, since the first electrode 102 and the second electrode 104 are disposed adjacently and are disposed within the first predetermined distance, the ECG component in the second input signal V2 is assumed to be the same as that in the first input signal V1 and hence is also denoted as ECG_1 in equation (2). And, M2 represents the noise component, especially motion artifact, shown in the second input signal V2.

Similarly, the second electrode group 12 of this embodiment can also have two electrodes 110 and 112 that may detect the third input signal V3 and the fourth input signal V4, respectively. The third input signal V3 and the fourth input signal V4 can be presented as the formulas listed below:

$$V3 = ECG\_3 + M3 \qquad (3)$$

$$V4 = ECG\_3 + M4 \qquad (4)$$

ECG_3 represents the ECG component in the third input signal V3; M3 represents the noise component, especially motion artifact, in the third input signal V3. In this embodiment, since the two electrodes 110 and 112 of the second electrode group 12 are disposed adjacently and are disposed within the second predetermined distance, the ECG component in the fourth input signal V4 is assumed to be the same as that in the third input signal V3 and hence is also denoted as ECG_3 in equation (4). And, M4 represents the noise component, especially motion artifact, shown in the fourth input signal V4.

As shown in the FIG. 1 and the FIG. 3, the processing module 14 is coupled to the first electrode group 10 through the first transmission line pair L1, and is coupled to the second electrode group 12 through the second transmission line pair L2. And the processing module 14 has a first calculating unit 140, a second calculating unit 142, a third calculating unit 144, and a fourth calculating unit 146. The first calculating unit 140 is coupled to the first transmission line pair L1 and the second transmission line pair L2 for receiving one of the input signals obtained by the first electrode group 10, such as the first input signal V1, and one of the input signals obtained by the second electrode group 12, such as the third input signal V3. The second calculating unit 142 is coupled to the first transmission line pair L1, and receives the first input signal V1 and the second input signal V2 obtained from the first electrode group 10. The third calculating unit 144 is coupled to the second transmission line pair L2, and receives the third input signal V3 and the fourth input signal V4 obtained from the second electrode group 12. The fourth calculating unit 146 is coupled to the first calculating unit 140, the second calculating unit 142, and the third calculating unit 144.

The first calculating unit 140 is configured to generate a body electrical signal VL2 according to the first input signal V1 and the third input signal V3. For example, the first calculating unit 140 calculates the difference between the first input signal V1 and the third input signal V3 to generate the body electrical signal VL2 accordingly. For example, the first calculating unit 140 can be, but is not limited to, a subtractor circuit or a DSP unit performing a mathematical formula. Therefore, the body electrical signal VL2 can be presented as the formula listed below:

$$VL2 = V1 - V3 \qquad (5)$$
$$= (ECG\_1 - ECG\_3) + (M1 - M3)$$
$$= ECG\_L2 + (M1 - M3)$$

ECG_L2 is the difference of the ECG components between the first input signal V1 and the third input signal V3, and can be considered as a lead signal which is not affected by noise. The noise component M1 and the noise component M2 are relevant to each other since the first electrode 102 and the second electrode 104 are disposed adjacently. In addition, the noise component M3 and the noise component M4 shall, similarly, be relevant to each other since the third electrode 110 and the fourth electrode 112 are disposed adjacently. Therefore, the relationship of the noise component M1 and the noise component M2, and the relationship of the noise component M3 and the noise component M4 may be presented as the formulas listed below:

$$M2 \approx \alpha M1 \qquad (6)$$

$$M4 \approx \beta M3 \qquad (7)$$

The second calculating unit 142 is configured to generate a first filtered signal y1 which is corresponding to the noise component M1 of the first input signal V1, wherein the noise component M1 represents motion artifact happened around the first electrode group 10. In one embodiment, the second calculating unit 142 includes a subtractor 1421, a variable filter 1422, and a filter coefficient update module 1423. The subtractor 1421 subtracts the second input signal V2 from the first input signal V1 so as to generate a first difference signal δM1. The variable filter 1422 has a p-th order finite impulse response structure with a first set of coefficients wn(0) to wn(p). The variable filter 1422 filters the first difference signal δM1 by convolving the first difference signal δM1 with the impulse response so as to generate the first filtered signal y1. According to formula (1) and (2) listed above, the first difference signal δM1 can be presented as the formula listed below:

$$\delta M1 = V1 - V2 \qquad (8)$$
$$= M1 - M2$$
$$= (1 - \alpha)M1$$

Similarly, the third calculating unit 144 is configured to generate a second filtered signal y2 which is corresponding to the noise component M3 of the third input signal V3, wherein the noise component M3 represents motion artifact happened around the second electrode group 12. In one embodiment, the third calculating unit 144 includes a subtractor 1441, a variable filter 1442, and a filter coefficient update module 1443. The subtractor 1441 subtracts the fourth input signal V4 from the third input signal V3 so as to generate a second difference signal δM2. The variable filter 1442 has a p-th order finite impulse response structure with a second set of coefficients wn_2(0) to wn_2(p). The variable filter 1442 filters the second difference signal δM2 by convolving the second difference signal δM2 with the impulse response so as to generate the second filtered signal y2. According to formula (3) and (4) listed above, the second difference signal M2 can be presented as the formula listed below:

$$\delta M2 = V3 - V4 \qquad (9)$$
$$= M3 - M4$$
$$= (1 - \beta)M3$$

The first filtered signal y1 corresponds to the noise component M1, and the second filtered signal y2 corresponds to the noise component M3. The fourth calculating unit 146 may include a subtractor for subtracting the first filtered signal y1 and the second filtered signal y2 from the body electrical signal VL2 generated by the first calculating circuit 140 so as to generate the lead signal ECG_L2.

In practice, the lead signal ECG_L2 can further be transmitted to the second calculating unit 142 and the third calculating unit 144, respectively, as a feedback signal. The filter coefficient update module 1423 of the second calculating unit 142 receives the lead signal ECG_L2 and the first difference signal δM1, and generates a first set of update coefficients delta_wn(0) to delta_wn(p). The filter coefficient update module 1423 then transmits the first set of update coefficients delta_wn(0) to delta_wn(p) to the variable filter 1422 to update the first set of coefficients wn(0) to wn(p) so as to generate a more accurate noise component M1 of the first input signal V1, denoted as y1'. Similarly, the filter coefficient update module 1443 of the third calculating unit 144 receives the lead signal ECG_L2 and the second difference signal δM2, and generates a second set of update coefficients delta_wn_2(0) to delta_wn_2(p). The filter coefficient update module 1443 then transmits the second set of update coefficients delta_wn_2(0) to delta_wn_2(p) to the variable filter 1442 to update the second set of coefficients wn 2_(0) to wn_2(p) so as to generate a more accurate noise component M3 of the third input signal V3, denoted as y2'.

After receiving a modified filtered signal y1' and a modified filtered signal y2', the fourth calculating unit 146 can generate a modified lead signal ECG_L2' with higher accuracy. Of course, the embodiment does not limit whether to retrieve the lead signal as the feedback signal or not.

In another embodiment of the invention, the first calculating unit 140 can further generate another body electrical signal VL2' which is different from the aforementioned body electrical signal VL2. For example, the body electrical signal VL2' can be presented as the formula listed below:

$$\begin{aligned}VL2' &= (V1-V3)+(V2-V4) \\ &= 2(ECG\_1-ECG\_3)+(1+\alpha)M1-(1+\beta)M3 \\ &= 2(ECG\_L2)+(1+\alpha)M1-(1+\beta)M3 \\ &= 2(ECG\_L2)+((1+\alpha)/\alpha)\delta M1-((1+\beta)/\beta)\delta M3\end{aligned} \quad (10)$$

In another embodiment, according to the formula (10), the first calculating unit 140 is configured to receive the first input signal V1, the second input signal V2, the third signal V3 and the fourth input signal V4 so as to generate the body electrical signal VL2' accordingly. For example, the first calculating unit 140 can be, but is not limited to, a subtractor circuit. The second calculating unit 142 is configured to generate the first filtered signal y1 which is corresponding to the noise component M1 of the first input signal V1, wherein the noise component M1 represents motion artifact happened around the first electrode group 10. The third calculating unit 144 is configured to generate the second filtered signal y2 which is corresponding to the noise component M3 of the third input signal V3, wherein the noise component M3 represents motion artifact happened around the second electrode group 12. The fourth calculating unit 146 includes a subtractor for subtracting the first filtered signal y1 and the second filtered signal y2 from the body electrical signal VL2' generated by the first calculating circuit 140 so as to generate the lead signal ECG_L2.

The processing module 14 attempts to eliminate the noise component of the body electrical signal by iteratively adjusting the coefficients of the variable filters 1422 and 1442. The process of iteratively adjusting the coefficients of the variable filters so as to provide more actuate noise component of the body electrical signal is known as convergence. A fast convergence indicates that the processing module 14 takes a short time to figure out the appropriate filter coefficients. In order to make the processing module 14 to convergence very soon, in one embodiment of the invention, one of the two input signals obtained from the electrode group is emphasized so as to make the two input signals obtained from the electrode group have greater difference. To emphasize the difference of input signals, the electrodes may have different size of contact area or different physical properties, e.g. wet electrode and dry electrode. So that the discrimination of the input signals, e.g. the first input signal V1 and the second input signal V2 may be increased.

Besides, the discrimination of the first input signal V1 and the second input signal V2 may also be increased by filtering them under different conditions. Similarly, the discrimination of the third input signal V3 and the fourth input signal V4 may also be increased by filtering them under different conditions.

Figure 4:
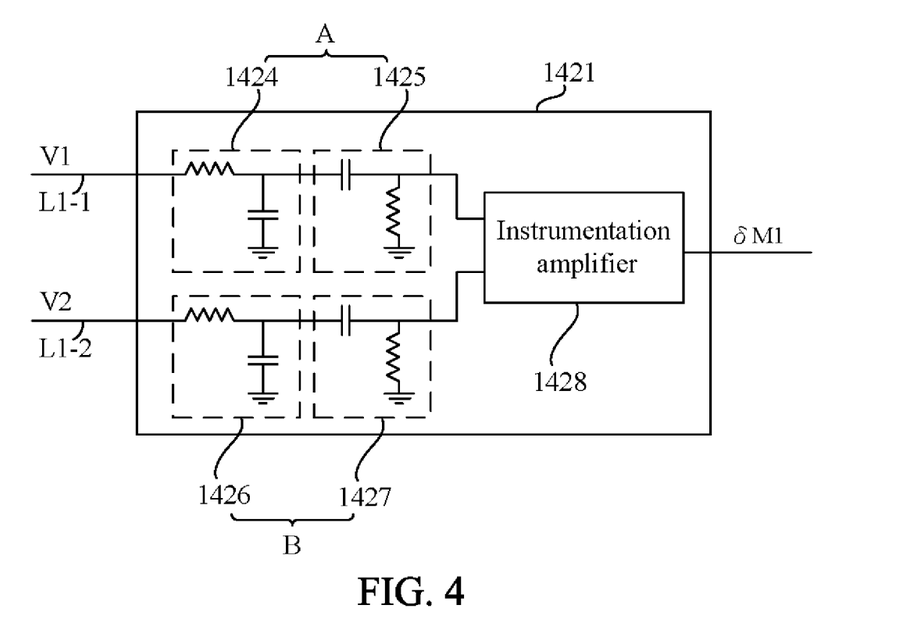
FIG. 4 shows a circuit diagram of a portion of a second calculating unit of the processing module of FIG. 3 according to an embodiment of the invention.

Please refer to FIG. 3 and FIG. 4. FIG. 4 shows an alternative implementation of the subtractor 1421 of the second calculating unit 142 according to an embodiment of the invention. As shown in FIG. 4, the subtractor 1421 includes a first modifying unit A, a second modifying unit B, and an instrumentation amplifier 1428. The first modifying unit A includes a low pass filter 1424 and a high pass filter 1425. The second modifying unit B includes a low pass filter 1426 and a high pass filter 1427.

The first modifying unit A is coupled to transmission wire L1-1 for receiving the first input signal V1, and generating a first modified signal. The second modifying unit B is coupled to transmission wire L1-2 for receiving the second input signal V2, and generating a second modified signal. The instrumentation amplifier 1428 is coupled to the first modifying unit A and the second modifying unit B for receiving the first modified signal and the second modified signal so as to generate the first difference signal δM1. To be noted, the subtractor 1441 of the third calculating unit 144 may be implemented using similar circuits as shown in FIG. 4.

Specifically, the first input signal V1 is filtered by the low pass filter 1424 and the high pass filter 1425 sequentially, and the second input signal V2 is filtered by the low pass filter 1426 and the high pass filter 1427 sequentially. To be noted, the frequency response of the low pass filter 1424 and that of the low pass filter 1426 shall be different. For example, the cut-off frequencies of the low pass filter 1424 may be 30 Hz, and the cut-off frequencies of the low pass filter 1426 may be 97 kHz. In addition, the frequency response of the high pass filter 1425 and that of the high pass filter 1427 shall be different. For example, the cut-off frequencies of the high pass filter 1425 may be 1 Hz, and the cut-off frequencies of the high pass filter 1427 may be 0.015 Hz. Thus, the first input signal V1 and second input signal V2 are modified by different modifying process so as to increase the discrimination of the first input signal V1 and the second input signal V2. Similarly, the third input signal V3 and fourth input signal V4 may be modified by different modifying process so as to increase the discrimination of the third input signal V3 and the fourth input signal V4.

Figure 5A:
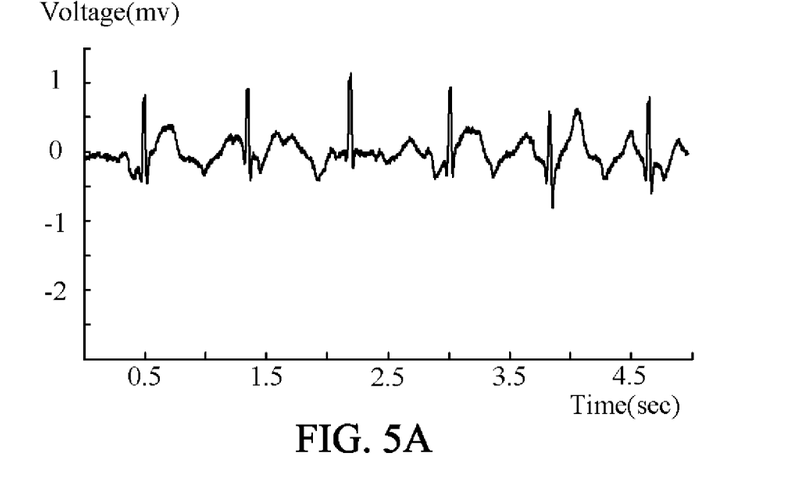
FIG. 5A shows an oscillogram of a body electrical signal according to an embodiment of the invention.

Here is an example about how to filter the motion artifact from the body electrical signal. Please refer to FIG. 3 and FIG. 5A. FIG. 5A shows an oscillogram of the body electrical signal according to an embodiment of the invention. As shown in figures, according to formula (5), the body electrical signal generated by the first calculating unit 140 is severely interfered with the noise, such as motion artifacts, respiration, or electrode noise. Thus, doctors may not be able to correctly analyze the waveform shape between successive beats of the body electrical signal, and may misdiagnose the level of cardiac stability accordingly.

Figure 5B:
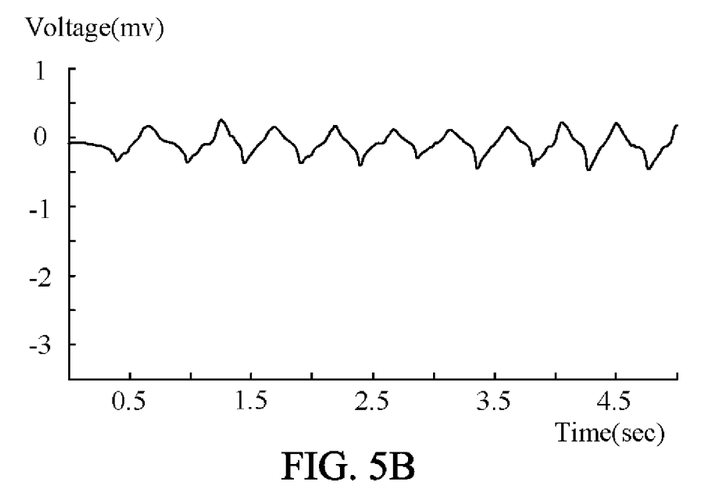
FIG. 5B shows an oscillogram of motion artifacts within the body electrical signal according to an embodiment of the invention.
Figure 5C:
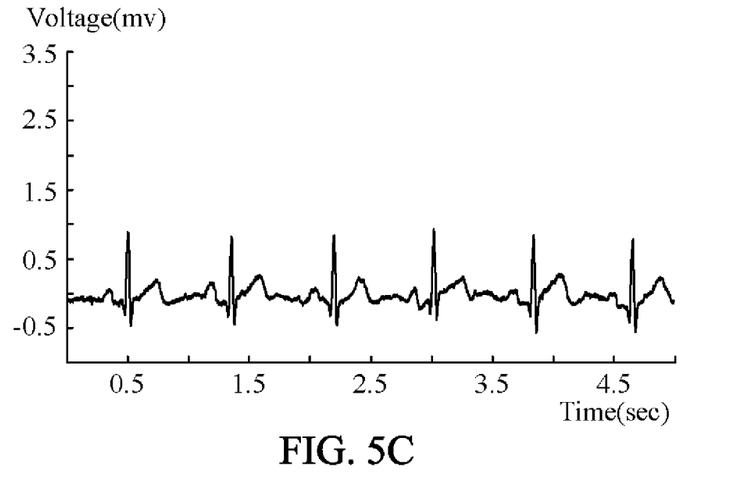
FIG. 5C shows an oscillogram of a lead signal according to an embodiment of the invention.

Please refer to FIG. 3 and FIG. 5B. FIG. 5B shows an oscillogram of motion artifacts within the body electrical signal according to an embodiment of the invention. As shown in figures, the second calculating unit 142 and the third calculating unit 144 can estimate the motion artifacts around the first electrode group 10 and the second electrode group 12. Please refer to FIG. 3 and FIG. 5C, FIG. 5C shows an oscillogram of the lead signal according to an embodiment of the invention. As shown in figures, the fourth calculating unit 146 eliminates the estimated noise shown in FIG. 5B from the body electrical signal shown in FIG. 5A to generate the lead signal shown in FIG. 5C. Clearly, the signal analyzing system 1 can greatly reduce the motion artifacts by utilizing the disclosed first electrode group 10, the second electrode group 12, and processing module 14.

Figure 6:
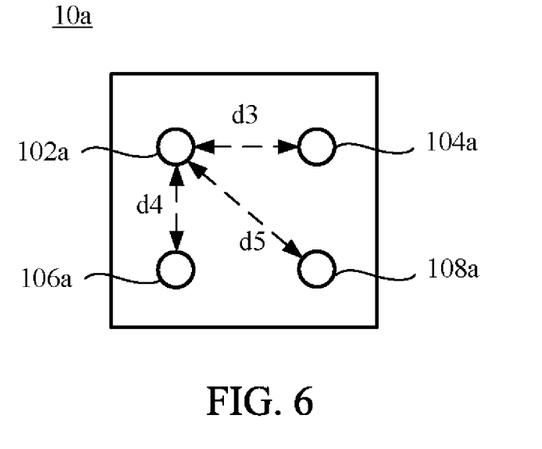
FIG. 6 shows a schematic diagram of the first electrode group according to another embodiment of the invention.

To be noted, each electrode group may have more than two electrodes, and can obtain more than two input signals correspondingly. Please refer to FIG. 6. FIG. 6 shows a schematic diagram of the first electrode group according to another embodiment of the invention. As shown in FIG. 6, the electrode group 10a can have 4 electrodes, such as an electrode 102a, an electrode 104a, an electrode 106a and an electrode 108a. The distance between the electrode 102a and the electrode 104a is denoted as distance d3. The distance between the electrode 102a and the electrode 106a is denoted as distance d4. The distance between the electrode 102a and the electrode 108a is denoted as distance d5. In practice, all of the distance d3, d4, and d5 may be less than the first predetermined distance, e.g. 1 cm or 1.5 cm.

Figure 7:
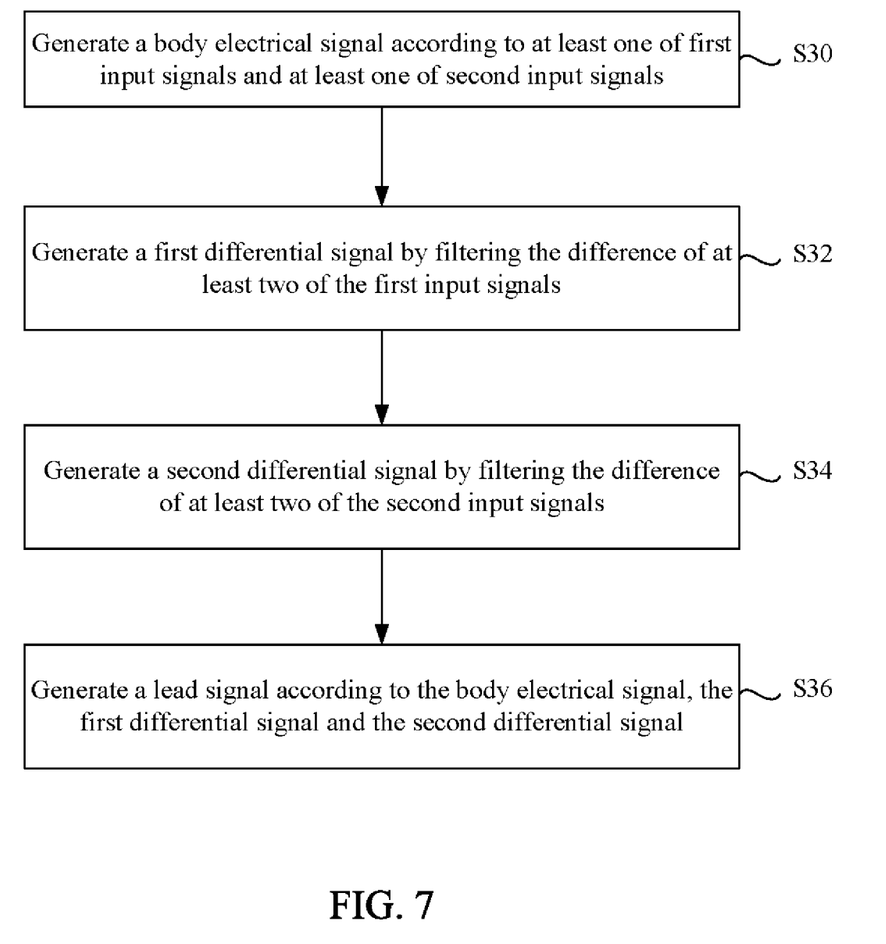
FIG. 7 shows a flow chart of a signal analyzing method according to an embodiment of the invention.

In order to explain how the signal analyzing system 1 works, please refer to FIG. 1, FIG. 3 and FIG. 7. FIG. 7 shows an example flow chart of a signal analyzing method according to an embodiment of the invention. As shown in figures, in step S30, the first calculating unit 140 generates a body electrical signal according to one of input signals transmitted through the transmission line L1 and one of input signals transmitted through the transmission line L2. In step S32, the second calculating unit 142 generates a first filtered signal for estimating the motion artifact around the first electrode group 10 by filtering the difference of the input signals obtained from the first electrode group 10. In step S34, the third calculating unit 144 generates a second filtered signal for estimating the motion artifact around the second electrode group 12 by filtering the difference of the input signals obtained from the second electrode group 12. In step S36, the fourth calculating unit 146 generates the lead signal by subtracting the first filtered signal and the second filtered signal from the body electrical signal.

To sum up, the embodiments of the invention disclose a method and a system for signal analyzing with a processing module which can reduce the noise components, especially motion artifacts, of the ECG signal. One of the advantages of the approach is that users can easily and correctly analyze the waveform shape between successive beats in the filtered ECG signal, and can avoid misdiagnosing the level of cardiac stability.

The descriptions illustrated supra set forth simply embodiments of the invention; however, the characteristics of the invention are by no means restricted thereto. All changes, alternations, or modifications conveniently considered by those skilled in the art are deemed to be encompassed within the scope of the invention delineated by the following claims.

What is claimed is:

1. A signal analyzing system, comprising:
a first electrode group, having a plurality of first electrodes, configured to transmit a plurality of first input signals;
a second electrode group, having a plurality of second electrodes, configured to transmit a plurality of second input signals; and
a processing module, comprising:
a first calculating unit, coupled to the first electrode group and the second electrode group for receiving at least one of the plurality of first input signals and at least one of the plurality of second input signals, configured to generate a body electrical signal according to at least one of the first input signals and at least one of the second input signals;
a second calculating unit, coupled to the first electrode group for receiving the plurality of first input signals, configured to generate a first filtered signal by filtering a first difference signal corresponding to the plurality of first input signals;
a third calculating unit, coupled to the second electrode group for receiving the plurality of second input signals, configured to generate a second filtered signal by filtering a second difference signal corresponding to the plurality of second input signals; and
a fourth calculating unit, coupled to the first calculating unit, the second calculating unit and the third calculating unit for receiving the body electrical signal, the first filtered signal and the second filtered signal, configured to generate a lead signal by subtracting the first filtered signal and the second filtered signal from the body electrical signal.

2. The signal analyzing system according to claim 1, wherein the plurality of first electrodes and the plurality of second electrodes are adapted to be attached to a human body and configured to detect electrocardiogram (ECG) signals, the plurality of first electrodes are disposed within a first predetermined distance, and the plurality of second electrodes are disposed within a second predetermined distance.

3. The signal analyzing system according to claim 1, wherein the second calculating unit further receives the lead signal, and the second calculating unit generates the subsequent first filtered signal according to the subsequent first difference signal and the lead signal.

4. The signal analyzing system according to claim 1, wherein the third calculating unit further receives the lead signal, and the third calculating unit generates the subsequent second filtered signal according to the subsequent second difference signal and the lead signal.

5. The signal analyzing system according to claim 1, wherein the first calculating unit receives the plurality of first input signals and the plurality of second input signals, and generates the body electrical signal according to a difference of a sum of the plurality of first input signals and a sum of the plurality of second input signals.

6. The signal analyzing system according to claim 1, wherein the processing module further comprises:
a first modifying unit having a first frequency response for filtering at least one of the first input signals; and
a second modifying unit having a second frequency response for filtering at least another one of the first input signals;
wherein the first frequency response and the second frequency response are different.

7. The signal analyzing system according to claim 1, wherein the first electrode group further comprises:
  a first type of electrodes configured to transmit at least one of the plurality of first input signals; and
  a second type of electrodes configured to transmit at least another one of the plurality of first input signals;
  wherein the first type electrodes and the second type of electrodes are different.

8. A processing module, comprising:
  a first calculating unit, coupled to a plurality of first electrodes and a plurality of second electrodes for receiving at least one of a plurality of first input signals obtained from the plurality of first electrodes and at least one of a plurality of second input signals obtained from the plurality of second electrodes, configured to generate a body electrical signal according to at least one of the first input signals and at least one of the second input signals;
  a second calculating unit, coupled to the first electrodes for receiving the plurality of first input signals, configured to generate a first filtered signal for estimating the motion artifact corresponding to the first electrodes by filtering a first difference signal corresponding to the plurality of first input signals;
  a third calculating unit, coupled to the second electrodes for receiving the plurality of second input signals, configured to generate a second filtered signal for estimating the motion artifact corresponding to the second electrodes by filtering a second difference signal corresponding to the plurality of second input signals; and
  a fourth calculating unit, coupled to the first calculating unit, the second calculating unit, and the third calculating unit for receiving the body electrical signal, the first filtered signal and the second filtered signal respectively, configured to generate a lead signal by subtracting the first filtered signal and the second filtered signal from the body electrical signal.

9. The processing module according to claim 8, wherein the plurality of first electrodes and the plurality of second electrodes are adapted to be attached to a human body and configured to detect electrocardiogram (ECG) signals, the plurality of first electrodes are disposed within a first predetermined distance, and the plurality of second electrodes are disposed within a second predetermined distance.

10. The processing module according to claim 8, wherein the second calculating unit further receives the lead signal, and the second calculating unit generates the subsequent first filtered signal according to the subsequent first difference signal and the lead signal.

11. The processing module according to claim 8, wherein and the third calculating unit further receives the lead signal, and the third calculating unit generates the subsequent second filtered according to the subsequent second difference signal and the lead signal.

12. The processing module according to claim 8, wherein the first calculating unit receives the plurality of first input signals and the plurality of second input signals, and generates the body electrical signal according to a difference of a sum of the plurality of first input signals and a sum of the plurality of second input signals.

13. The processing module according to claim 8, further comprising:
  a first modifying unit having a first frequency response for filtering at least one of the first input signals; and
  a second modifying unit having a second frequency response for filtering at least another one of the first input signals;
  wherein the first frequency response and the second frequency response are different.

14. The signal analyzing system according to claim 1, wherein the second calculating circuit comprises:
  a first subtractor, for calculating a difference between two of the plurality of first input signals to generate the first difference signal;
  a first variable filter, coupled to the first subtractor, for filtering the first difference signal to generate the first filtered signal; and
  the third calculating circuit comprises:
  a second subtractor, for calculating a difference between two of the plurality of second input signals to generate the second difference signal;
  a second variable filter, coupled to the second subtractor, for filtering the second difference signal to generate the second filtered signal.

15. A signal analyzing method performed by a processing module of a system comprising a first electrode group and a second electrode group, wherein the first electrode group has a plurality of first electrodes configured to transmit a plurality of first input signals, and the second electrode group has a plurality of second electrodes configured to transmit a plurality of second input signals, and the signal analyzing method comprises:
  receiving at least one of the plurality of first input signals and at least one of the plurality of second input signals, and generating a body electrical signal according to at least one of the first input signals and at least one of the second input signals;
  receiving the plurality of first input signals, and generating a first filtered signal by filtering a first difference signal corresponding to the plurality of first input signals;
  receiving the plurality of second input signals, and generating a second filtered signal by filtering a second difference signal corresponding to the plurality of second input signals; and
  receiving the body electrical signal, the first filtered signal and the second filtered signal, and generating a lead signal by subtracting the first filtered signal and the second filtered signal from the body electrical signal.

16. The signal analyzing method according to claim 15, wherein the plurality of first electrodes and the plurality of second electrodes are adapted to be attached to a human body and configured to detect electrocardiogram (ECG) signals, the plurality of first electrodes are disposed within a first predetermined distance, and the plurality of second electrodes are disposed within a second predetermined distance.

17. The signal analyzing method according to claim 15, further comprising:
  receiving the lead signal, and generating the subsequent first filtered signal according to the subsequent first difference signal and the lead signal.

18. The signal analyzing method according to claim 15, further comprising:
  receiving the lead signal, and generating the subsequent second filtered signal according to the subsequent second difference signal and the lead signal.

19. The signal analyzing method according to claim 15, wherein the step of receiving at least one of the plurality of first input signals and at least one of the plurality of second input signals, and generating a body electrical signal according to at least one of the first input signals and at least one of the second input signals comprises:

receiving the plurality of first input signals and the plurality of second input signals, and generating the body electrical signal according to a difference of a sum of the plurality of first input signals and a sum of the plurality of second input signals.

20. The signal analyzing method according to claim 15, further comprising:

using a first modifying unit having a first frequency response to filter at least one of the first input signals; and using a second modifying unit having a second frequency response to filter at least another one of the first input signals;

wherein the first frequency response and the second frequency response are different.

21. The signal analyzing method according to claim 15, wherein the first electrode group further comprises:

a first type of electrodes configured to transmit at least one of the plurality of first input signals; and a second type of electrodes configured to transmit at least another one of the plurality of first input signals;

wherein the first type electrodes and the second type of electrodes are different.

\* \* \* \* \*